United States Patent [19]
Van Oort

[11] Patent Number: 5,647,347
[45] Date of Patent: Jul. 15, 1997

[54] MEDICAMENT CARRIER FOR DRY POWDER INHALATOR

[75] Inventor: Michiel M. Van Oort, Durham, N.C.

[73] Assignee: Glaxo Wellcome Inc., Research Triangle Park, N.C.

[21] Appl. No.: 328,578

[22] Filed: Oct. 21, 1994

[51] Int. Cl.$^6$ ................................................ A61M 15/00
[52] U.S. Cl. .......................... 128/203.15; 128/203.12
[58] Field of Search ................. 128/203.15, 203.19, 128/203.21, 203.23, 200.23

[56] References Cited

U.S. PATENT DOCUMENTS

| | | | |
|---|---|---|---|
| 2,642,063 | 6/1953 | Brown | 128/203.15 |
| 4,371,101 | 2/1983 | Cane et al. | 222/636 |
| 4,841,964 | 6/1989 | Hurka et al. | 128/203.15 |
| 4,955,945 | 9/1990 | Weick | 128/203.21 |
| 5,101,838 | 4/1992 | Schwartz et al. | |
| 5,388,572 | 2/1995 | Mulhauser et al. | 128/203.15 |
| 5,388,573 | 2/1995 | Mulhauser et al. | 128/203.12 |
| 5,394,869 | 3/1995 | Covarrubias | 128/203.21 |
| 5,415,162 | 5/1995 | Casper et al. | 128/203.21 |

FOREIGN PATENT DOCUMENTS

| | | |
|---|---|---|
| 9200115 | 1/1992 | European Pat. Off. . |
| 9420164 | 9/1994 | European Pat. Off. . |
| 4020571 | 1/1992 | Germany . |
| WO94/17679 | 8/1984 | WIPO . |
| WO90/13328 | 11/1990 | WIPO . |
| 24166 | 12/1993 | WIPO .............. 128/203.15 |

Primary Examiner—V. Millin
Assistant Examiner—William J. Deane, Jr.
Attorney, Agent, or Firm—Richard E. Jenkins; James P. Riek

[57] ABSTRACT

A medicament carrier for use in a dry powder inhalator device wherein the medicament carrier has at least one carrier screen portion. The carrier screen portion defines a plurality of interstices therein and carries a powdered medicament which is loaded onto the carrier screen portion surface such that the interstices of the carrier screen portion at least partially open and free of the dry powdered medicament.

10 Claims, 5 Drawing Sheets

MEDICAMENT CARRIER FOR DRY POWDER INHALATOR

FIELD OF THE INVENTION

The present invention relates to a medicament carrier, and more particularly to a carrier containing a dry powder medicament thereon and which is adapted to be positioned within a dry powder inhalator.

RELATED ART

Asthma and other respiratory diseases are typically treated by the inhalation of an appropriate medicament for deposition in the lungs to ease patient breathing and increase air capacity. The most widely used treatments for respiratory diseases have been (1) the inhalation of a medicament from a drug solution or suspension in a metered dose aerosol, pressurized inhalator and (2) the inhalation of a powdered drug (generally admixed with an excipient) from a dry powder inhalator. However, in view of recent evidence of the link between chlorofluorocarbon emissions and the deterioration of the earth's atmospheric ozone layer, use of drugs in pressurized inhalators is less desirable and interest in dry powder inhalation systems has substantially increased.

Applicant is presently aware of several different basic methods in use to provide fine particle powders to the respiratory tract without the use of undesirable chlorofluorocarbon propellants. The first method utilizes hard gelatin capsules which contain both a dose of the active material and, in addition, potential adjuvants. The inhalator used by the asthmatic patient for this method comprises a device for perforating or opening the capsule which is then inserted into the inhalator when needed. An air stream generated by the patient on a mouthpiece of the inhalator serves to remove the powder contained within the opened capsule. The empty capsule is then expelled from the inhalator, which is then ready to receive the next capsule. The air stream which passes through the capsule during inhalation acts to remove the powdered medicament from the broken capsule, but it has been found that the air stream created by the patient using this type of inhalator is generally not sufficient in duration to remove all of the contents from the capsule. Dry powder inhalators using this technology are disclosed in a number of prior art references including U.S. Pat. Nos. 3,906,950; 4,013,075; 3,807,400; and 3,991,761.

Another type of inhalator device is loaded with a package having a number of blisters which are spaced apart from each other. Each blister contains a fixed quantity of powdered medicament for administration to the patient. As each blister is moved into a predetermined position, it is broken by a suitable means so as to release the powder which is in turn inhaled by the patient. However, it has been found that moisture ingress into the blister pack can cause agglomeration of the prepared medicament therein. Consequently, when the prepared medicament is inhaled by the user, the preferred particle size for greatest efficacy in respiratory disease treatment may not necessarily be achieved. Moreover, the operation of the device requires the use of excipients (e.g., lactose) in order to meter and administer the medicament. This type of inhalation device is disclosed in a number of prior art patent publications including EPO Patent Application Publications Nos. EPO 211595; EPO 455463; and EPO 467172 A1.

Yet another type of dry powder inhalator contains a quantity of medicament therein which is sufficient for multiple doses. A representative example of this type of device is the Draco TURBUHALER® which is disclosed in U.S. Pat. Nos. 4,668,218; 4,667,668; and 4,805,811. The inhalator includes a device for withdrawing powdered medicament from the container and for preparing a dose for inhalation. The withdrawal and dose preparation includes a plate having a predetermined thickness and a number of cup-shaped holes therethrough. The plate can be moved by mechanical means from a position where a proportion of the holes are filled with powdered medicament taken from the container to another position in which the holes filled with the medicament are located within a channel. Air flows into the channel as a result of suction provided by the patient on a mouthpiece in fluid communication with the channel so as to remove the powdered medicament from the holes. However, it has been found that when suction is applied to entrain the medicament from one or more holes in the plate, not all of the medicament is entrained in the air flow. Moreover, the TURBUHALER® device is designed to administer large doses and is prone to significant variations in drug delivery.

A fourth dry powder inhalator device is disclosed in German Patent No. 4020571 A1 wherein a velour or velvet-type material loaded with powder is introduced into a jet stream of air. The airstream acts to lift the powder from the velour-like material and to entrain the powder within the airstream which is then in turn inhaled by the patient. One shortcoming of this type of inhalator device is that there is a tendency for the carrier fibers to intermix with the medicament.

A new type of carrier disc for a dry powder inhalator which has recently been proposed is disclosed in U.S. patent application Ser. No. 08/025,964 filed Mar. 3, 1993 (priority application of PCT Publication No. WO 94/20164, published Sep. 15, 1994, to Mulhauser et al.) which teaches a screen mesh disc which is impregnated at spaced locations or portions along its circumference with a dose of powdered medicament, such as salmeterol hydroxynapthoate, which can be useful in the treatment of asthma. Since the powdered medicament is impregnated into the interstices of the screen portions, the air impinging upon the screen portions and the powdered medicament during inhalation will cause the medicament to break up so as to aerosol or atomize the medicament. Further, the interstitial deposit of the medicament on the screen portions allows turbulent air to surround each medicament dose and entrain it to assist complete dispensing of the medicament dose from the screen portions into the airstream. However, the use of the screen disc in the dry powder inhalator device also suffers certain shortcomings including imprecise metering of the powdered medicament since the screen portion interstices are used to meter the medicament. Other shortcomings of the interstitial deposit of the powdered medicament (or impregnation of the medicament) into the screen portions are limitations of dose size to interstitial volume, and the necessity to deaggregate large clusters of medicament present in interstitial voids.

Applicant's present invention avoids many of the problems associated with prior art dry powder inhalators by providing a novel medicament carrier which allows a predetermined and precise dose of the dry powdered medicament to be supplied through the inhalator device upon demand. Moreover, applicant's invention provides much greater flexibility in medicament dose range with a specific carrier screen portion size since the medicament dose is not dependent on the interstitial void volume of the carrier screen portion.

SUMMARY OF THE INVENTION

In accordance with the present invention, a medicament carrier is provided which is adapted for use in a dry powder inhalator device and includes at least one carrier screen portion defining a plurality of interstices therein and loaded with at least one dose of a powdered medicament. The powdered medicament is loaded onto the carrier screen portion surface such that the interstices thereof are at least partially open and free of the powdered medicament.

Also, in accordance with an alternative embodiment of the present invention, a medicament carrier for use in a dry powder inhalator device is provided which comprises two spaced-apart screens wherein each screen defines a plurality of interstices therein. A plurality of substantially spherical substrate elements are positioned between the two screens which are loaded with at least one dose of a powdered medicament such that the powdered medicament is removed from the surface of the spherical substrate elements when an air flow is introduced through the two spaced-apart screens of the medicament carrier.

It is therefore the object of the present invention to provide a medicament carrier for use in a dry powder inhalator which provides for administration of a predetermined precise dosage of the powdered medicament.

It is another object of the present invention to provide a medicament carrier for use in a dry powder inhalator device which provides for the ingested particle size of the powdered medicament dose to be formed for maximum beneficial efficiency.

Some of the objects of the invention being stated, other objects will become evident as the description proceeds, when taken in connection with the accompanying drawings described hereinbelow.

Figure 1:
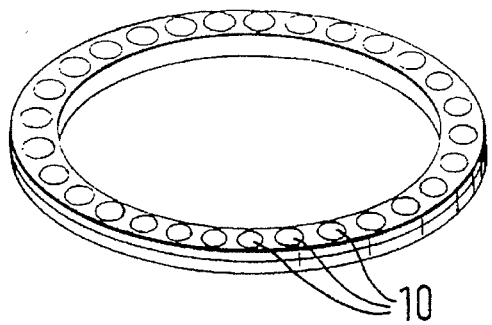
FIG. 1 is a perspective view of a first representative medicament carrier cassette for use in a dry powder inhalator device in accordance with the present invention.
Figure 2:
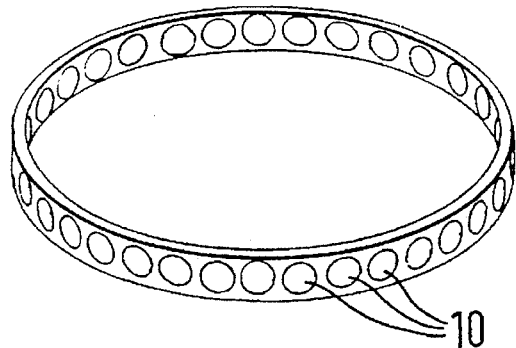
FIG. 2 is a perspective view of a second representative medicament carrier cassette for use in a dry powder inhalator device in accordance with the present invention.
Figure 3:
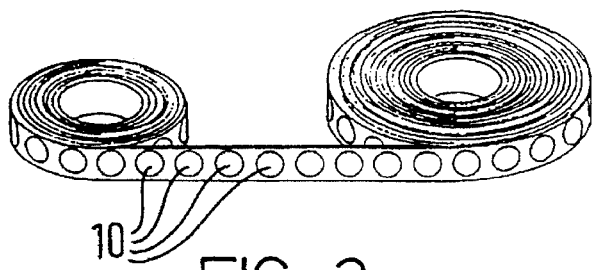
FIG. 3 is a perspective view of a third representative medicament carrier cassette for use in a dry powder inhalator device in accordance with the present invention.
Figure 4:
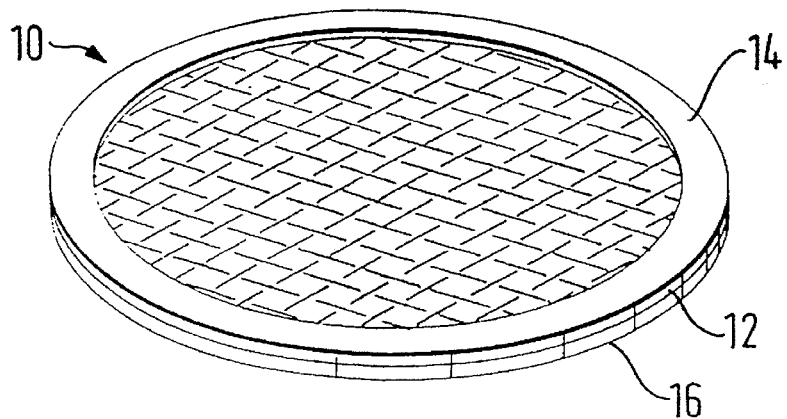
FIG. 4 is a perspective view of an individual medicament carrier such as utilized in the representative cassettes shown in FIGS. 1–3.
Figure 5:
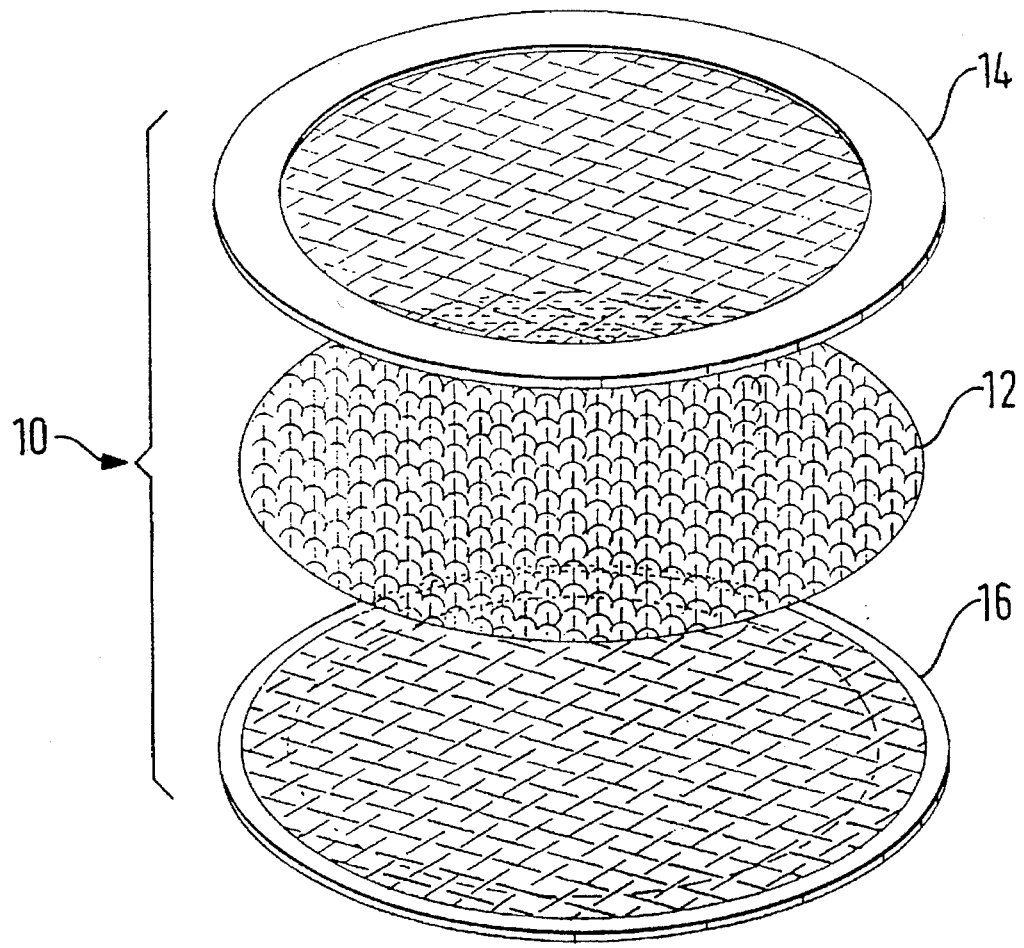
FIG. 5 is an exploded perspective view of the medicament carrier shown in FIG. 4.
Figure 6:
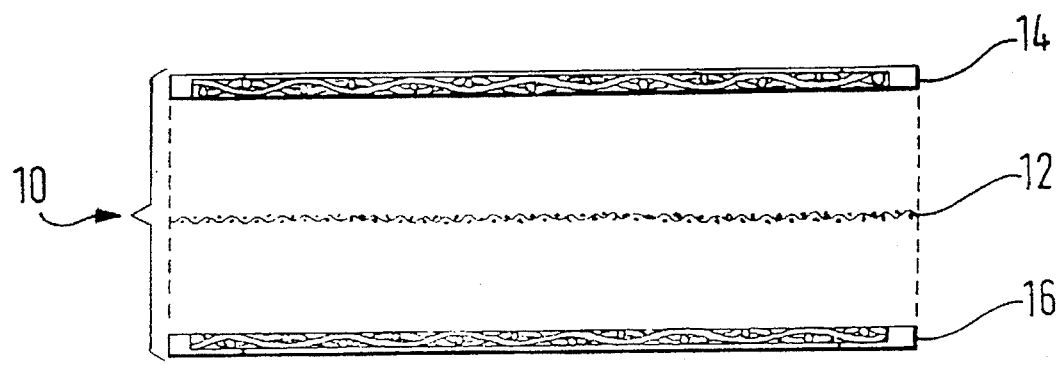
FIG. 6 is an exploded vertical cross-sectional view of the medicament carrier shown in FIG. 4.
Figure 7:
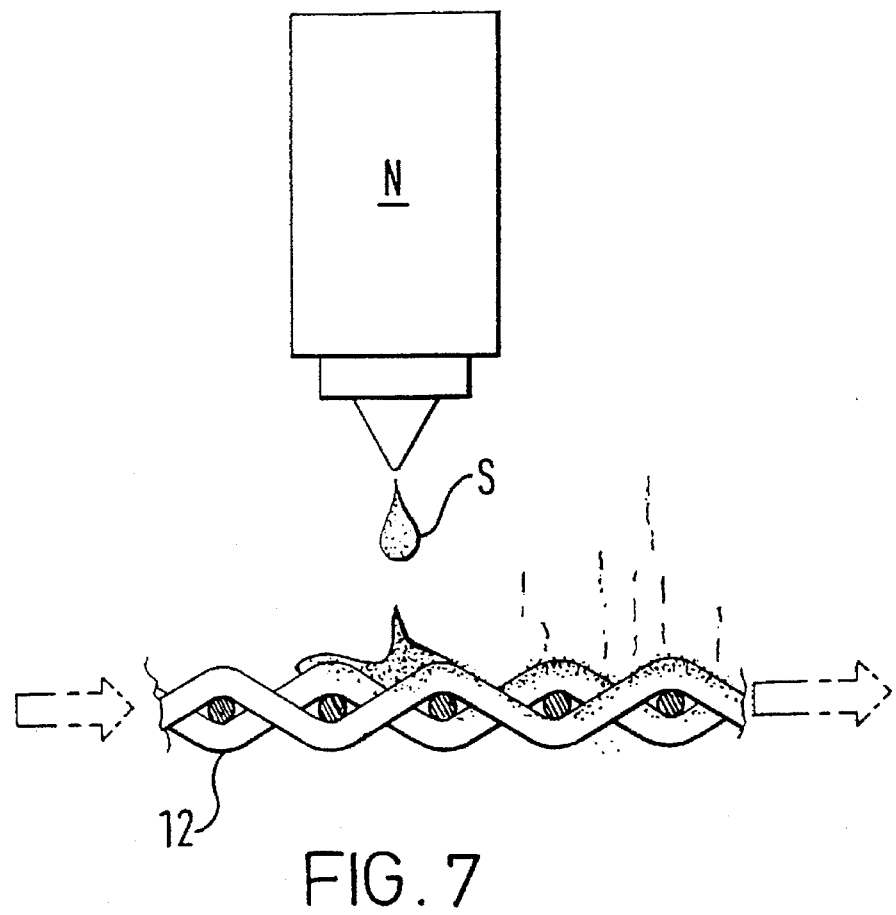
FIG. 7 is a schematic view illustrating application of a suspension solution of a powdered medicament being applied to the medicament carrier screen portion shown in FIGS. 5 and 6;

FIG. 8 is an enlarged, perspective view showing loading of the powdered medicament onto the medicament carrier screen portion surface after evaporation of the suspending agent such that the interstices of the medicament carrier screen portion are at least partially open and free of the powdered medicament;

FIG. 9 illustrates the medicament carrier of the present invention and the effect thereupon when subjected to an inhalation air pulse;

FIGS. 10A and 10B show a plan view and an enlargement of a selected portion thereof, respectively, of a medicament carrier screen portion with an accreted powdered medicament loaded thereon; and FIG. 11 illustrates a second embodiment of the medicament carrier of the present invention wherein the carrier comprises two spaced-apart screens having a plurality of substantially spherical substrate elements positioned therebetween which are loaded with powdered medicament and the effect thereupon when subjected to an inhalation air pulse.

BEST MODE FOR CARRYING OUT THE INVENTION

Referring now to FIGS. 1–11 of the drawings wherein like numerals indicate like elements throughout the several views, three (3) embodiments of medicament carrier cassettes are illustrated in FIGS. 1–3 which each include a number of spaced-apart medicament carriers 10 therein which form the subject of the instant invention. Powdered medicaments which can be used with the medicament carrier of the present invention for inhalation therapy of systemic absorption via the respiratory tract include, but are not limited to, albuterol, terbutaline, isoproterenol, metaprotaranol, pirbuterol, salmeterol hydroxynapthoate, fluticasone propionate, budesonide, beclomethasone dipropionate, and triacetonide. Moreover, it is understood that the powdered medicaments may optionally be admixed with excipients such as lactose and glucose.

Referring more specifically to the drawings, medicament carriers 10 are shown in FIGS. 4–6. Medicament carriers 10, a plurality of which are included in each of representative medicament carrier cassettes of FIGS. 1–3, are formed from carrier screen portions 12 which most suitably are secured or sandwiched between enclosure screens 14 and 16, although screens 14 and 16 would not be required in other embodiments of medicament carriers 10 in accordance with the present invention. It should be appreciated that medicament carrier cassettes of FIGS. 1–3 are configured so as to be insertable into any suitable breath-activated dry powder inhalator (not shown) such as are well known in the art and that novel medicament carriers 10 of the present invention could be incorporated into many other types of sheets, plates, discs and the like in addition to the three depicted representative cassettes.

The carrier screen portion 12 can be a non-woven or woven screen formed from natural or synthetic fibers or stamped from a metal blank or photoacid etched from stainless steel or ceramic or formed in any other suitable fashion, so as to provide a plurality of interstices 12A (see FIG. 8) therein. Applicant's invention provides for depositing a prescribed dose of a dry powdered medicament substantially on the surface of carrier screen portion 12 (see FIG. 8) and not primarily within the interstices 12A thereof. The size of the dose depends upon the drug used. For example, a common drug used for asthmatics is salmeterol hydroxynapthoate which is normally dispensed in single doses of about 50 micrograms (μg). Thus, each medicament dose of such a drug could be deposited on the surface of a selected carrier screen portion 12 which is most suitably formed so as to be about 0.06–0.25 inches in diameter in size and to have interstices therein measuring approximately 0.0005 inches or more in width. As noted hereinbefore, carrier screen portion 12 may be formed in many ways including a non-woven or woven screen formed from natural or synthetic fibers or stamped from a metal blank or photoacid etched from stainless steel or ceramic material.

Carrier screen portion 12 is formed with interstices 12A of approximately 0.0005 inches or more in width and (optionally) is secured or sandwiched between enclosure screens 14 and 16 so as to form medicament carrier 10. It is to be understood that medicament carrier 10 could be formed exclusively from carrier screen portion 12 as a matter of design choice in forming medicament carrier 10. A plurality of medicament carriers 10 are positioned on the perimeter of a medicament carrier cassette such as the rings shown in FIGS. 1 and 2, respectively, or along the length of a medicament carrier cassette tape such as shown in FIG. 3. Optional enclosure screens 14 and 16 each permit access of an external air flow or air pulses through the exposed area of medicament carrier 10 when the carrier is positioned within a suitable dry powder inhalator device (not shown) so that the powdered medicament can be entrained in the air (see FIG. 9) which is then inhaled by the patient through the inhalator mouthpiece (not shown) which communicates with the air flow. By suitable mechanical or electromechanical means, medicament carriers 10 within medicament carrier cassettes such as shown in FIGS. 1–3 are selectively indexed to present a new dose of a powdered medicament to the air flow or air pulse of the inhalator device.
Figure 8:
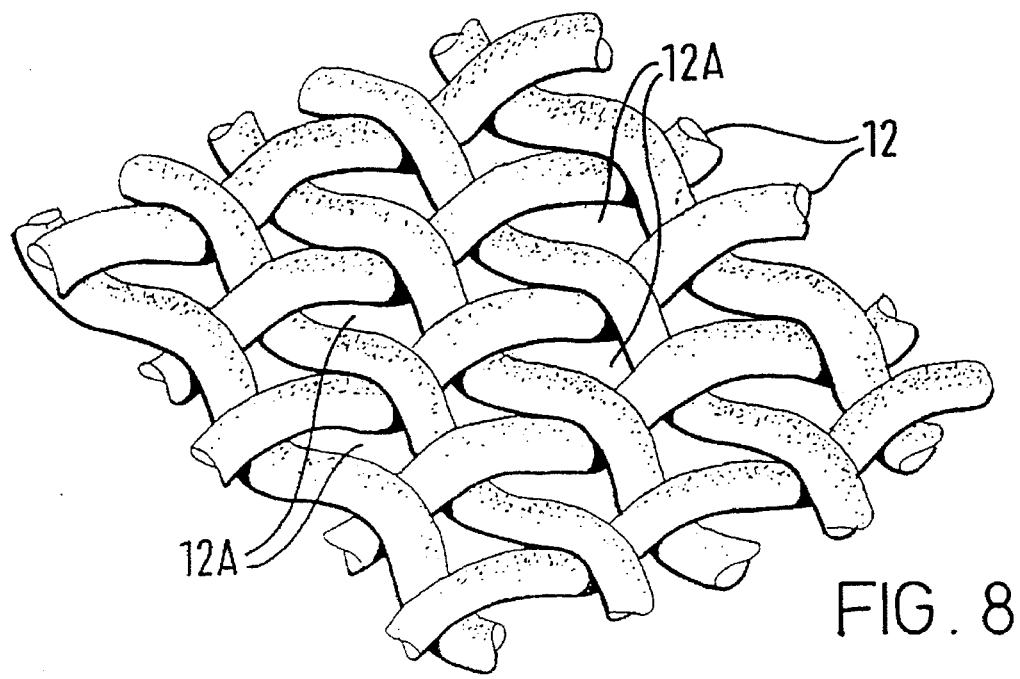
Figure 9:
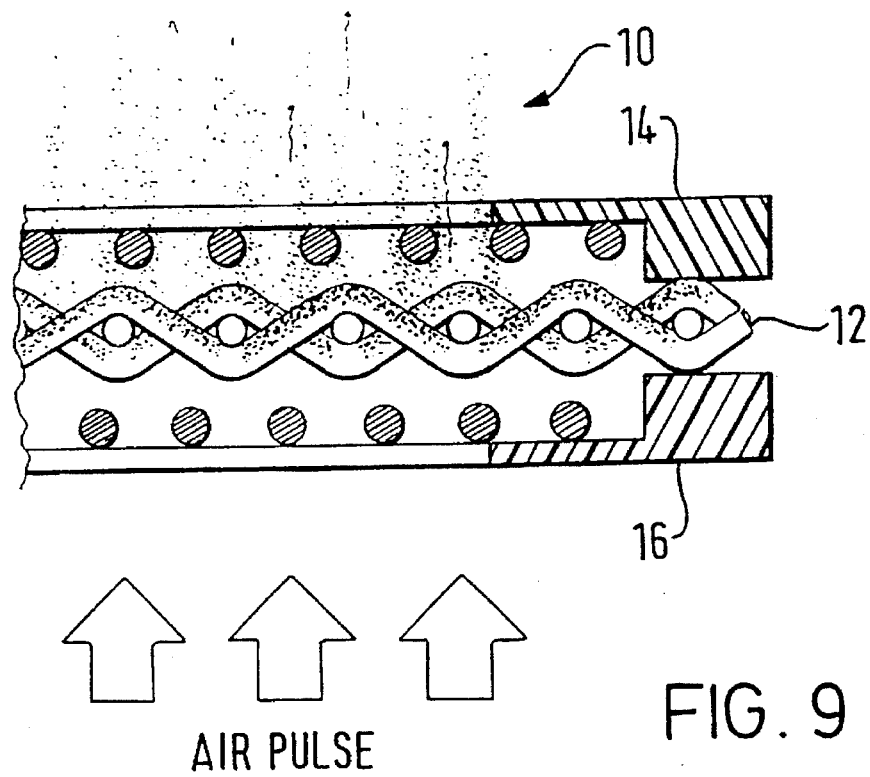

Since the powdered medicament is primarily deposited on the surface of carrier screen portion 12 and spans a significant number of interstices of carrier screen portion 12 (see FIG. 8), the number of particles in physical contact with each other is significantly reduced and therefore the amount of energy required to deaggregate the particles into the respirable particle size range is minimized (as opposed, for example, to strictly interstitial deposit of the powdered medicament). The thickness of the layer of powdered medicament on the surface of the elements forming carrier screen portion 12 can be selected so as to minimize the degree of particle-particle contact and/or the size of particle microclusters. The air pulse directed at the dry powdered medicament will serve to sweep the dose of powdered medicament off of carrier screen portion 12, to suck the dose off of carrier screen portion 12 by virtue of the Bernoulli effect and/or to burst through the dose bridging the interstices.

Figure 10A:
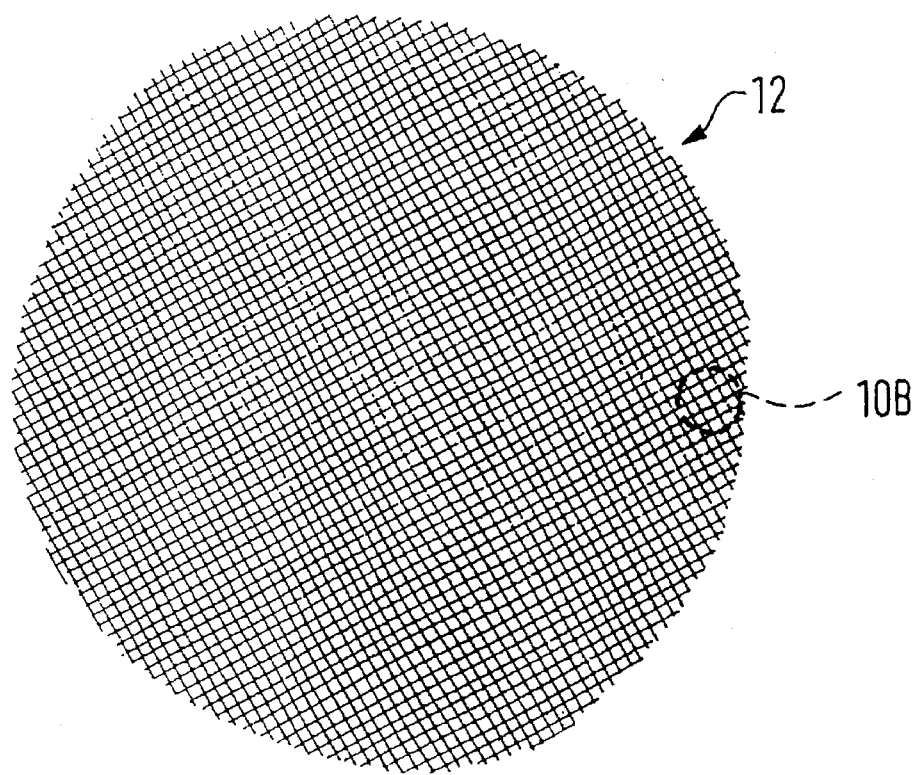
Figure 10B:
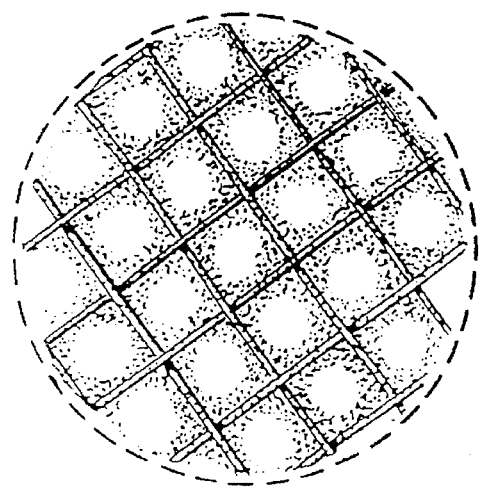

Applicant has discovered that the high shear forces and turbulence experienced by the deposited powdered medicament will result in removal and/or deaggregation of the particles or microclusters of the particles. Thus, each interstice 12A of carrier screen portion 12 will act as a nozzle or jet if any particles are not directly adhered to the surface of the elements defining carrier screen portion 12 but are accreted thereto (see, for example, FIGS. 10A and 10B).

Screen 14 (which, as previously noted, is optional and not a required element of the medicament carrier of the invention) is utilized so as to further aid in the deaggregation of the drug particles due to impaction and high shear forces resulting from contact of the powdered medicament (removed by the air flow from carrier screen portion 12 and entrained in the air flow therethrough) with screen 14. Also, upstream screen 16 serves to modify the air flow so as to maximize turbulence and shear to facilitate deaggregation of the powdered medicament.

Figure 11:
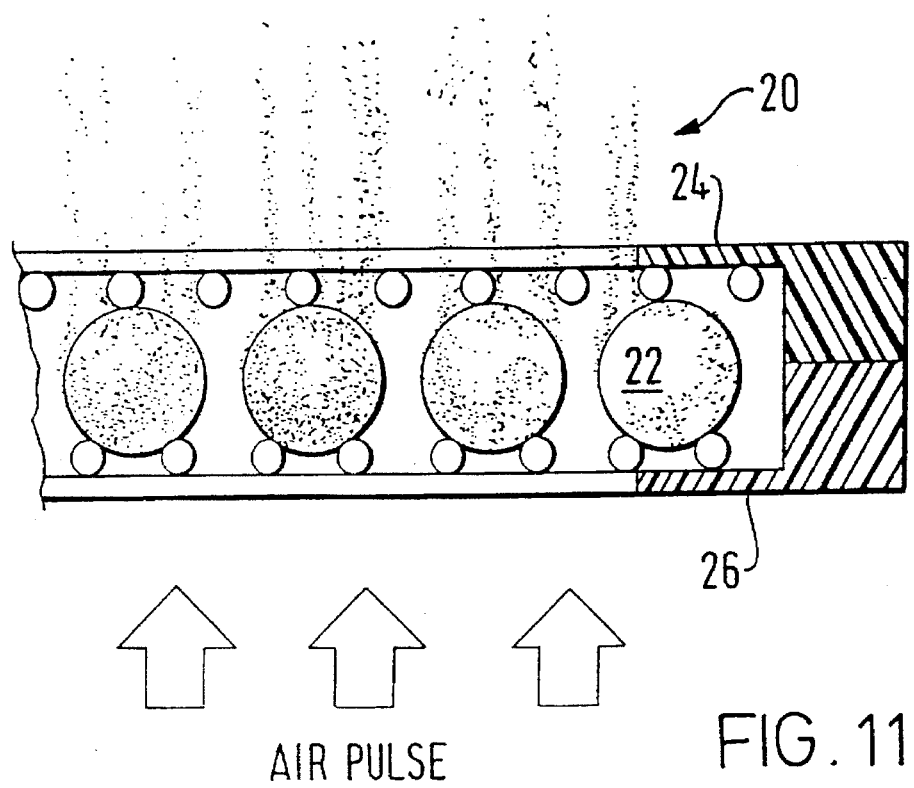

An alternative embodiment of applicant's invention contemplates providing medicament carrier 20 (see FIG. 11), which does not require deposition of dry powder medicament directly onto the surface of the elements defining carrier screen portions 12. Alternative embodiment medicament carrier 20 comprises substantially spherical substrate elements 22 formed from materials such as organic or inorganic materials such as metals, polymers or polysaccharides and upon the surfaces of which the dry powdered medicament is deposited. Spherical substrate elements 22 are carried between two screen elements 24 and 26 so as to position spherical substrate elements 22 in the air flow or air pulse through the exposed area of medicament carrier 20 within the air flow channel of an inhalator so that the dry powder medicament can be entrained in the air or aerosolized for inhalation by a patient. Medicament carrier 20 is positioned with an inhalator device (not shown) so that the interstices of screen elements 24 and 26 serve functionally as air jets in order to facilitate deaggregation and removal of the dry powdered medicament from the surfaces of spherical substrate elements 22.

Experimental Testing

Applicant utilized an extensive survey to select an appropriate suspending medium for dry powder medicament to be applied to the carrier screen portions of the drug carriers of a medicament carrier cassette (e.g., sheet, plate, disc, tape or the like having a plurality of medicament carrier screen portions therein). The selection criteria can include non-flammability, non-toxicity, a boiling point close to room temperature (for high vapor pressure and low energy input to remove the liquid), and low environmental impact. Applicant found perfluoropentane to be a good suspension medium which has significant advantages over many other liquids, although other suspending medium may be used in the practice of the present invention. Micronized salmeterol dry powder medicament may be easily suspended in perfluoropentane, and at refrigerated temperatures the perfluoropentane-salmeterol suspensions appear to be stable for several days.

Applicant studied a number of screen materials for use as the carrier screen portions of the medicament carrier cassette, etc. Physio-chemical properties of the screen material which are important include moisture content, abrasion/heat/chemical resistance, dimensional stability, physical properties of the screen (such as percent open area, air permeability), thread diameter and weave type. Screen samples for use as carrier screen portions were studied including nylon, polyester, polypropylene and stainless steel, and applicant presently believes stainless steel and non-hygroscopic polymers are preferred screen materials since moisture is a problem with many dry powder medicament formulations. Thus, the screen material should be relatively non-hygroscopic and hydrophobic, and this fact decreases the likelihood of nylon and polyester being suitable screen materials. Polypropylene, ethylene tetrafluoroethylene (ETFE) and E-CTFE are non-hygroscopic and have excellent hydrophobicities and thus should be suitable screen materials for forming the carrier screen portions of the medicament carriers of the invention.

Although other types of screens may be used as discussed in some detail hereinabove, stainless steel-type screens were used in the testing to be described in more detail below.

Testing Results

Applicant's preliminary statistically designed experiments utilized stainless steel carrier screens and investigated the following factors: mesh count (180, 230, 325; same wire diameter, different percentage open area), drug loading (50 µg and 250 µg), dot size (0.1, 0.15, 0.2 inches), air pulse pressure (2.0, 3.5 and 5.0 atmospheres), air pulse volume (0.1, 0.2 and 0.3 milliliters) and screen configuration (air pulse impacts the drug first—DF, the screen first—SF, and twin screens—TS). Dot size is understood to be the carrier screen diameter.

A 2.5% suspension of fluticasone propionate in perfluoropentane was prepared, and the drug was dispensed or filled onto the screens using an EPPENDORF brand electronic pipette. The particle sizing was accomplished by placing the appropriate screen into the test inhalation dispersing apparatus and firing the dose into an API brand AEROSIZER time-of-flight particle size analyzer.

Summarily, the test results reveal that the best results were obtained by applying the dry powdered medicament to the medicament carrier of the invention using a single screen (no enclosure screens 14 and 16) with high air volume, high air pressure, low drug loading and a small dot size. However, on average the highest particle counts were obtained with a small dot, high drug loading and twin screen configuration.

When the three screen configurations were analyzed separately, applicant discovered that a coarse mesh carrier screen portion worked better for single screen (no enclosure screens 14 and 16) configurations, while a fine mesh performed better for the twin screen (including enclosure screen 14) configuration.

Applicant's analysis performed on only the high air volume/high air pressure measurements confirm the fact that a single screen configuration, low drug loading and a small dot size provided the most favorable particle size distributions, while a twin screen with a high drug loading produced the highest particle counts. Additionally, the fine screen mesh tended to provide higher particle counts on the average.

Applicant's test results from which the aforementioned observations were obtained are set forth in Table 1 and Table 2 below.

TABLE I

TESTING RESULTS
DRUG LOADING = 40 μg
AIR PRESSURE = 70 psig
AIR VOLUME = 0.3 mL

| Config. | MMAD (μM) | % < 6.3 μm | Counts |
|---|---|---|---|
| DF | 2.3 | 98.5 | 262734 |
| SF | 2.5 | 97.2 | 342523 |
| TS | 6.7 | 49.3 | 752301 |

NOTE: The results were averaged over screen mesh and dot size

TABLE 2

TESTING RESULTS
DRUG LOADING = 175 μg
AIR PRESSURE = 70 psig
AIR VOLUME = 0.3 mL

| Config. | MMAD (μm) | % < 6.3 μm | Counts |
|---|---|---|---|
| DF | 4.0 | 71.2 | 1090524 |
| SF | 3.5 | 76.2 | 699456 |
| TS | 11.4 | 22.6 | 1704059 |

NOTE: The results were averaged over screen mesh and dot size

It will be understood that various details of the invention may be changed without departing from the scope of the invention. Furthermore, the foregoing description is for the purpose of illustration only, and not for the purpose of limitation—the invention being defined by the claims.

What is claimed is:

1. A medicament carrier for use in a dry powder inhalator device comprising a carrier having at least one carrier screen portion defining a plurality of interstices therein and loaded with at least one dose of powdered medicament particles of predetermined particulate size, wherein the powdered medicament particles are loaded onto the carrier screen portion surface from a suspension of the medicament particles and suspending agent and the suspending agent is evaporated such that the interstices of the carrier screen portion surface are at least partially open and free of the powdered medicament particles.

2. The medicament carrier according to claim 1, wherein said screen portion is formed from a material selected from the group consisting of non-woven screens, woven screens, stamped metal blanks, photoacid etched stainless steel, and photoacid etched ceramic.

3. The medicament carrier according to claim 1, wherein said carrier comprises a plurality of carrier screen portions each loaded with one dose of the powdered medicament particles.

4. The medicament carrier according to claim 1, wherein the interstices in said carrier screen mesh portion are at least 0.0005 inches in width.

5. The medicament carrier according to claim 1, wherein the powdered medicament particles loaded on said carrier screen portion are selected from the group consisting of albuterol, terbutaline, isoproterenol, metaprotaranol, pirbuterol, salmeterol hydroxynapthoate, fluticasone propionate, budesonide, beclomethasone dipropionate, and triacetonide.

6. The medicament carrier according to claim 1, wherein at least one screen is positioned adjacent but spaced apart from said carrier to facilitate deaggregation of the powdered medicament particles.

7. The medicament carrier according to claim 6, wherein said at least one screen comprises two screens with one screen positioned adjacent but spaced apart from each side of said carrier to facilitate deaggregation of the powdered medicament particles.

8. A medicament carrier for use in a dry powder inhalator device comprising a carrier having at least one carrier portion comprising two spaced apart screens wherein each defines a plurality of substantially spherical substrate elements positioned between said screens and loaded with at least one dose of powdered medicament particles of predetermined particulate size from a suspension of the medicament particles and suspending agent and the suspending agent is evaporated, wherein the powdered medicament particles are removed from the spherical substrate elements and entrained in an air flow introduced through the two spaced apart screens.

9. The medicament carrier according to claim 8, wherein the surface of said plurality of spherical substrate elements is loaded with one dose of powdered medicament particles.

10. The medicament carrier according to claim 8, wherein the powdered medicament loaded onto said spherical substrate elements is selected from the group consisting of albuterol, terbutaline, isoproterenol, metaprotaranol, pirbuterol, salmeterol hydroxynapthoate, fluticasone propionate, budesonide, beclomethasone dipropionate, and triacetonide.

* * * * *